US00PP10260P

United States Patent [19]

Cosner et al.

[11] Patent Number: Plant 10,260

[45] Date of Patent: Feb. 24, 1998

[54] DOUBLE IMPATIENS PLANT NAMED 'TIOGA HOT PINK'

[76] Inventors: Harlan B. Cosner; Sue L. Cosner, both of P.O. Box 173, Broadbent, Oreg. 97414

[21] Appl. No.: 777,908

[22] Filed: Dec. 20, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of Double Impatiens plant named 'Tioga Hot Pink', characterized by its large hot pink flowers; flowers held above or beyond the foliage; consistently double and symmetrical flower form; numerous flowers per plant; freely branching, dense plant habit; upright and outwardly spreading plant habit; and dark green foliage.

1 Drawing Sheet

The present invention relates to a new and distinct cultivar of Double Impatiens plant, botanically known as *Impatiens walleriana*, and hereinafter referred to by the cultivar name 'Tioga Hot Pink'.

The new cultivar is a product of a planned breeding program conducted by the inventors in Coquille, Oreg. The objective of the breeding program was to develop varieties with attractive flower colors, consistently double flower form, uniform plant habit, and numerous flowers per plant.

The new cultivar originated from a cross made in July, 1992, by the inventors of an unnamed proprietary seedling selection as the male or pollen parent with an unnamed proprietary seedling selection as the female or seed parent.

The cultivar 'Tioga Hot Pink' was discovered and selected by the inventors as a flowering plant within the progeny of the stated cross in a controlled environment in Coquille, Oreg. Asexual reproduction of the new cultivar by terminal cuttings taken at Coquille, Oreg., has shown that the unique features of this new Double Impatiens are stable and reproduced true to type in successive generations of asexual reproduction.

The following traits have been repeatedly observed and are determined to be the unique characteristics of 'Tioga Hot Pink'. These characteristics in combination distinguish the new Double Impatiens as a new and distinct cultivar:

1. Large hot pink flowers.
2. Flowers held above or beyond the foliage.
3. Consistently double and symmetrical flower form.
4. Numerous flowers per plant.
5. Freely branching, dense plant habit.
6. Upright and outwardly spreading plant habit.
7. Dark green foliage.

In constrast to plants of the new Double Impatiens, plants of the parent proprietary seedling selections have semi-double flowers with reproductive organs and capable of producing seed. In addition, the male parent has deep rose-colored flowers and bronze foliage; and the female parent has light pink flowers and leaves that are 20% larger than the new Double Impatiens.

The new Double Impatiens is similar in flower color to the Double Impatiens cultivar Rosebud Rose (not patented). However in side-by-side comparisons in Coquille, Oreg., under commercial practice, plants of the new Double Impatiens differed from plants of the cultivar Rosebud Rose in the following characteristics:

1. Plants of the new Double Impatiens are more uniform in plant habit than plants of the cultivar Rosebud Rose.

2. Plants of the new Double Impatiens are more freely branching and have stronger lateral branches than plants of the cultivar Rosebud Rose.

3. Leaves of plants of the new Double Impatiens are smaller than leaves of plants of the cultivar Rosebud Rose.

4. Flowers of plants of the new Double Impatiens face upward or outward whereas flowers of plants of the cultivar Rosebud Rose face outward or downward as peduncles of plants of the cultivar Rosebud Rose are weaker than peduncles of the new Double Impatiens.

5. Flower spurs of plants of the new Double Impatiens are light pink in color whereas flower spurs of plants of the cultivar Rosebud Rose are light green in color.

A detailed comparison of plants of the new Double Impatiens and the cultivar Rosebud Rose appears in Chart A at the end of the specification.

The new Double Impatiens has not been observed under all possible environmental conditions. The phenotype may vary significantly with variations in environment such as temperature and light level, without, however, any variance in genotype.

The accompanying colored photographs illustrate the overall appearance and flower color of the new Double Impatiens, showing the colors as true as it is reasonably possible to obtain in colored reproductions of this type.

The first photograph comprises a side perspective view of a typical plant of the new Double Impatiens.

The second photographc comprises a side perspective view of typical plants of the cultivar Rosebud Rose (left) and the new Double Impatiens (right) showing the differences in plant and flowering habit. Flower and foliage colors in the photographs may appear different from the actual colors due to light reflectance.

The following observations, measurements, values, and comparisons describe plants grown in Coquille, Oreg., grown under double layer of polyethylene with day temperatures ranging from 23 to 30C and night temperatures ranging from 10 to 18C, and light levels ranging from 3,000 to 5,000 footcandles.

In the following description, color references are made to The Royal Horticultural Society Colour Chart except were general terms of ordinary dictionary significance are used.

Botanical classification: *Impatiens walleriana* cultivar 'Tioga Hot Pink'.

Parentage:

*Male or pollen parent.*—Unnamed proprietary seedling selection.

*Female or seed parent.*—Unnamed proprietary seedling selection.

Propagation:

*Type cutting.*—Terminal cuttings.

*Time to initiate roots.*—About 14 days at a temperature of 20 C.

*Rooting habit.*—Numerous, fibrous, and well-branched.

Plant description:

*Form.*—Upright and outwardly spreading, triangular.

*Growth habit.*—Moderately vigorous. Dense and bushy growth. Flowers above or beyond the foliage. Suitable for 10 to 25-cm containers.

*Plant height.*—About 23 cm.

*Branching habit.*—Freely branching with about eight lateral branches, branches strong.

*Lateral branches.*—Size: Length: About 20 cm. Diameter: About 9 mm. Internode length: About 2.5 cm. Color: 144A with red spots and areas at nodes, 59A.

*Foliage description.*—Leaves simple, generally symmetrical, abundant, alternate, and flat in aspect. Size, largest leaves: Length: About 4.5 cm. Width: About 3 cm. Shape: Ovate with acute apex, attenuate base and crenate margin. Texture: Smooth. Color: Upper surface: 147A. Lower surface: 147B/147C. Venation, upper surface: 147B. Venation, lower surface: 147B/147C. Petiole: Size: Length: About 2 cm. Diameter: About 2 mm. Color: White to light green.

Flower description:

*Flower type and habit.*—Large hot pink flowers. Consistently double and symmetrical flowers. Freely and continuously flowering. Flower buds open similar to a rose in fullness. Flowers arise from leaf axils, terminal bud opening first. Usually six flowers per lateral branch. Flowers positioned above or beyond the foliage and face upward or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 1.3 cm.

*Flowers buds.*—Size: Length: About 1.3 cm. Diameter: About 1 cm. Shape: Ovoid. Color: 62A.

*Petals/petaloids.*—Quantity: Numerous. Size (largest petals): Length: About 1.6 cm. Width: About 1.6 cm. Shape: Round with rounded apex, cuneate or obtuse base and entire margin. Texture: Satiny, smooth. Color: When opening, upper surface: Iridescent, 57A. When opening, lower surface: Iridescent, 62A. Mature, upper surface: Iridescent, 57A. Mature, lower surface: Iridescent, 62A. Fading to: Iridescent, 57A.

*Spur.*—Length: About 2 cm. Shape: Narrow and curved. Color: Light pink.

*Peduncles.*—Length: About 2.5 cm. Angle: Upright to outwardly arching. Strength: Moderate. Color: 146B.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance nor susceptibility to pathogens has not been observed.

CHART A

| CHARACTERISTIC | TIOGA HOT PINK | ROSEBUD ROSE |
|---|---|---|
| PLANT SHAPE | Upright and outwardly spreading, triangular | Open center, irregular habit, roughly triangular |
| BRANCHING HABIT | Freely, about 8 lateral branches per plant, branches strong | Low to moderate, about 5 lateral branches per plant, branches weak and cascade from weight of foliage and flowers |
| LATERAL BRANCH LENGTH | About 20 cm | About 25 cm |
| LATERAL BRANCH DIAMETER | About 9 mm | About 7 mm |
| LATERAL BRANCH STRENGTH | Strong | Weak, stems cascade |
| LEAF LENGTH | About 4.5 cm | About 5.5 cm |
| LEAF WIDTH | About 3 cm | About 3.5 |
| PETIOLE LENGTH | About 2 cm | About 1.75 cm |
| FLOWERING HABIT | Upward or outward facing | Outward or downward facing |
| SPUR LENGTH | About 2 cm | About 3 cm |
| SPUR COLOR | Light pink | Light green |
| PETAL COLOR, WHEN OPENING, LOWER SURFACE | 57A | 57A |
| PETAL COLOR, WHEN OPENING, UPPER SURFACE | 62A | 65A |
| PETAL COLOR, MATURE, LOWER SURFACE | 57A | 57A |
| PETAL COLOR, MATURE, UPPER SURFACE | 62A | 62C/62D |
| PEDUNCLE ANGLE | Upright to outwardly arching | Bent from weight of flowers |
| PEDUNCLE STRENGTH | Moderate | Weaker |

It is claimed:

1. A new and distinct Double Impatiens plant named 'Tioga Hot Pink', as illustrated and described.

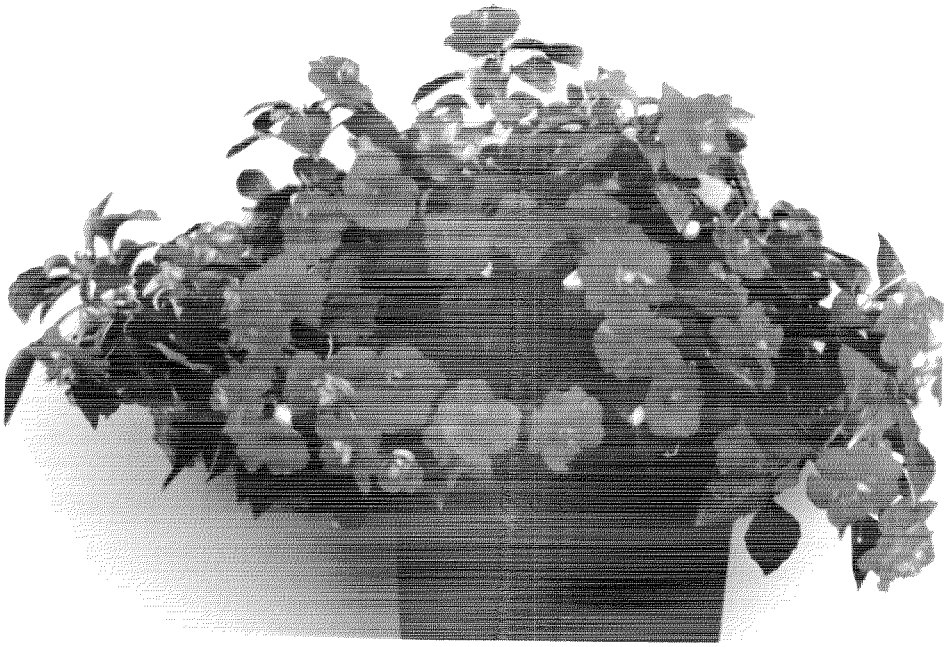
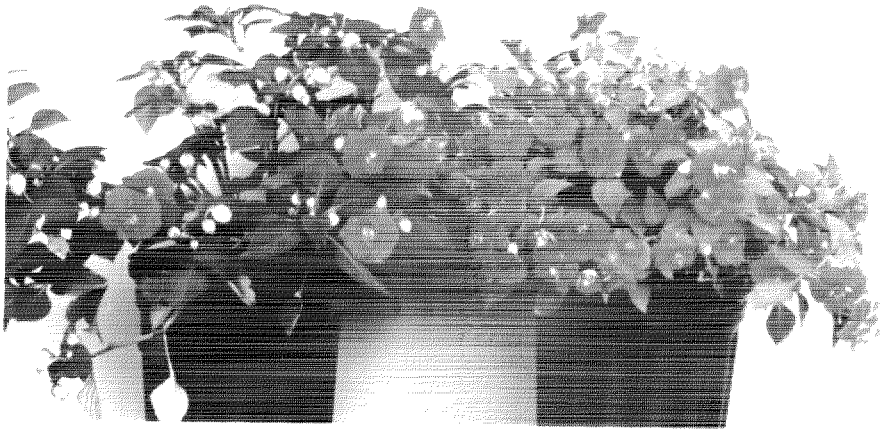

* * * * *